United States Patent [19]
Cuine et al.

[11] Patent Number: 5,334,392
[45] Date of Patent: Aug. 2, 1994

[54] MATRIX TABLET PERMITTING THE SUSTAINED RELEASE OF INDAPAMIDE AFTER ORAL ADMINISTRATION

[75] Inventors: Alain Cuine, Saint Jean de Braye; Bruno H. de Barochez, Chevilly; David Guez, Neuilly sur Seine, all of France

[73] Assignee: Adir et Compagnie, Courbevoie, France

[21] Appl. No.: 895,787

[22] Filed: Jun. 9, 1992

[30] Foreign Application Priority Data

Jun. 18, 1991 [FR] France .................. 91 07400

[51] Int. Cl.$^5$ .......................... A61K 9/20; A61K 9/16
[52] U.S. Cl. .................... 424/468; 424/486; 424/488; 424/501; 424/499; 514/929
[58] Field of Search ............... 424/484, 486, 488, 464, 424/465, 468, 470, 501; 514/929, 414

[56] References Cited

U.S. PATENT DOCUMENTS

| | | | |
|---|---|---|---|
| 3,565,911 | 2/1971 | Beregi et al. | 548/483 |
| 4,716,041 | 12/1987 | Kjornaes et al. | 424/470 |
| 4,812,316 | 3/1989 | Rossi | 424/468 |
| 5,004,613 | 4/1991 | Radebaugh et al. | 424/468 |

OTHER PUBLICATIONS

Dorland's Illustrated Medical Dictionary, 24th Edition, W. B. Saunders Company, Philadelphia and London, 1965, p. 707 and cover sheet.

*Primary Examiner*—Edward Webman
*Attorney, Agent, or Firm*—Gordon W. Hueschen

[57] ABSTRACT

The invention relates to a matrix tablet for the sustained release of indapamide which ensures a continuous and uniform release of the active principle after oral administration.

9 Claims, 5 Drawing Sheets

MATRIX TABLET PERMITTING THE SUSTAINED RELEASE OF INDAPAMIDE AFTER ORAL ADMINISTRATION

The subject of the present invention is a matrix tablet permitting the sustained release of indapamide, ensuring uniform and constant blood levels after absorption of the galenic form by the oral route.

Indapamide, a compound of formula (I):

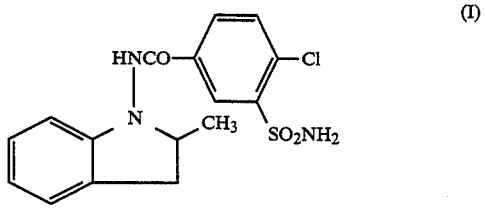

is a non-thiazidic sulphamide derivative with an antihypertensive property at the usual doses administered to humans.

Indapamide has been, up until now, administered by the oral route at a dose of 2.5 mg per day by means of an immediate-release form.

Now, an immediate-release form can lead, in certain patients, to considerable blood peaks. A sustained-release form allows these blood peaks to be avoided and a uniform blood concentration to be obtained in humans. This makes it possible to reduce the undesirable effects, which can arise as a result of the "peak effect", accompanied by hydroelectrolytic-type and metabolic-type disorders linked to variations in the plasma levels of the active principle.

A sustained-release form of indapamide therefore ensures a better therapeutic index in the treatment of essential arterial hypertension.

To do this, a sustained release over time, in a precisely controlled manner, must be ensured. The speed of release must be reproducible and correlated with the blood concentrations observed after administration.

Among the mechanisms which may be employed to control the diffusion of a soluble active principle, the diffusion of the active principle through a gel formed after the swelling of a hydrophilic polymer brought into contact with dissolving liquid (*in vitro*) or gastro-intestinal fluid (in vivo) may be cited as a principal one.

Many polymers have been described as capable of forming this gel. The principal ones are the derivatives of cellulose, in particular the cellulose ethers such as hydroxypropyl cellulose, hydroxymethyl cellulose, methyl cellulose or methyl hydroxypropyl cellulose, and among the different commercial grades of these ethers are those showing fairly high viscosities. It should be noted that the systems described do not theoretically allow a zero order in the kinetic release equation to be reached.

The manufacturing processes commonly employed for the manufacture of such matrix tablets are either direct compression, after mixing the different excipients and active principle(s), or wet granulation.

BRIEF DESCRIPTION OF THE DRAWINGS

Reference is now made to the accompanying drawings for a better understanding of the invention, wherein.

Figure 1:
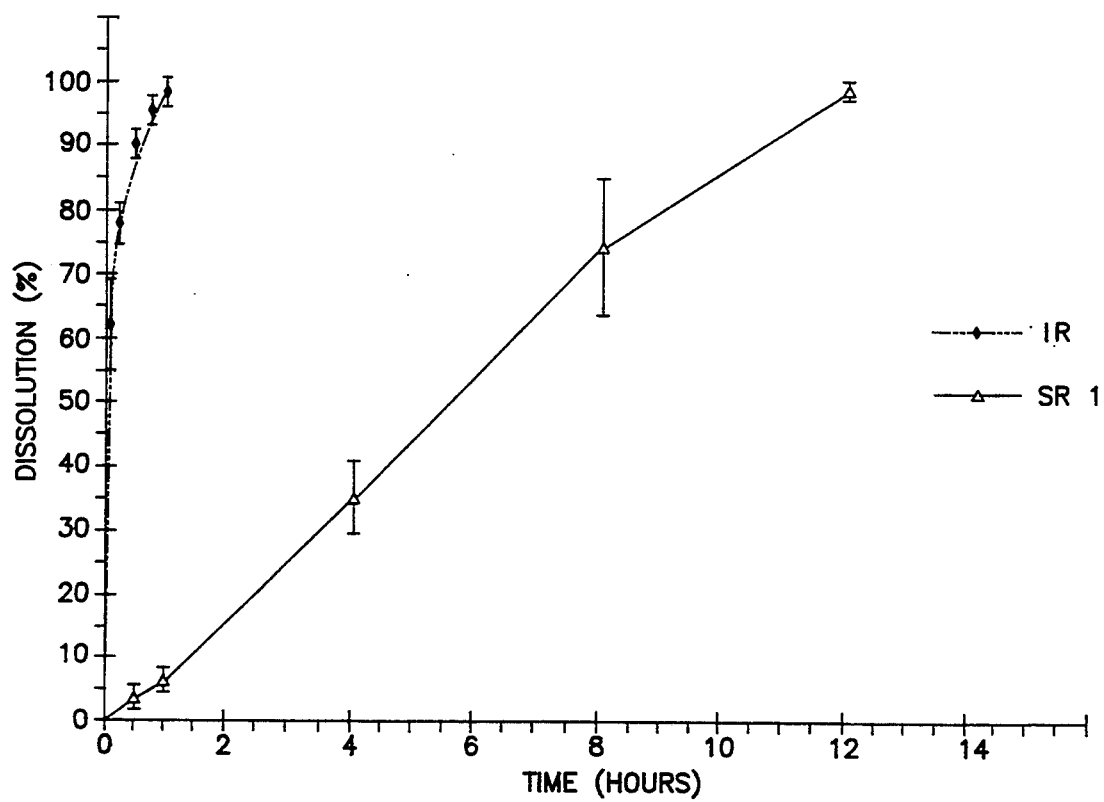
FIG. 1 is a dissolution profile comparing an immediate-release form of an indapamide tablet with a sustained-release form of an indapamide tablet according to the present invention and Example 1 hereof.

The matrix tablet described in the present invention combines, in a novel manner, two polymers of different chemical families, which allows a precisely controlled release of the active principle. Furthermore, this combination is perfectly suited to the physicochemical properties of indapamide.

This controlled release is linear for more than eight hours and is such that 50 per cent of the total quantity of indapamide is released over a period of between 5 and 14 hours. Moreover, the matrix tablet according to the invention allows a sustained release of indapamide resulting in blood levels in humans of between 20 and 80 ng/ml, 24 hours at the most after administration of the tablet. The unit dosage can thus vary according to the age and the weight of the patient or the nature and the severity of the ailment. Generally, it ranges between 1 and 2.5 mg for a daily course of treatment.

The first polymer is a high-viscosity methyl hydroxypropyl cellulose, the second is a polyvidone. The combination of these two polymers allows release kinetics *in vitro* which are linear (of zero order) for more than 8 hours. The percentage of polymer derived from cellulose is between 30 and 50% of the total mass of the tablet, while that derived from polyvidone is between 2 and 10% of the total mass of the tablet.

These two polymers are used separately in the tablet in order to ensure, in a reproducible manner, control of the release of the active principle. A novel manufacturing process has itself been developed so that each polymer used in the formulation can play its part in the most effective manner possible with the advantages of the two processes of wet granulation and direct compression.

A wet granulation is carried out with the polyvidone, in order to create, around the active principle, a hydrophilic environment favorable for its good dissolution, and also so as to obtain the most uniform unit dosage possible, the indapamide content of the finished tablet being approximately 1 percent. Lactose, a hydrophilic diluent, is employed to this end, namely, to create the hydrophilic environment mentioned.

After this granulation stage, a direct compression mixture is made and then tableted.

The examples which follow illustrate the invention but do not limit it in any way. The preparation of the sustained-release tablets is carried out according to the manufacturing process which follows:

Stage A: Mixing of indapamide, the polyvidone and the lactose, then wetting of this mixture by means of an aqueous/alcoholic solution. The wet mass prepared is then granulated, dried and then graded, so as to obtain a granulate whose physical characteristics allow good filling of the dies of a fast tableting machine.

Stage B: Mixing of the granulate obtained in stage A with methyl hydroxypropyl cellulose.

Stage C: Lubrication of the mixture obtained in stage B with colloidal silica and magnesium stearate.

Stage D: Compression of the lubricated mixture obtained in stage C in a rotary tableting machine, so as to obtain tablets having a hardness, measured by diametrical crushing, of approximately 60 to 75 N.

EXAMPLE 1

A sustained-release tablet (SR 1) is prepared by employing the formula given in Table 1, following the operating procedure of stages A to D.

TABLE 1

Unit formula of the SR 1 tablet

| Compound | Quantity (mg) |
| --- | --- |
| Indapamide | 2.5 |
| Lactose | 114.9 |
| Polyvidone** | 6.2 |
| Methylhydroxypropylcellulose* | 59.0 |
| Magnesium stearate | 2.0 |
| Colloidal silica | 0.4 |

The dissolution profile *in vitro* of this form (SR 1) is shown in FIG. 1 (appended).

Figure 2:
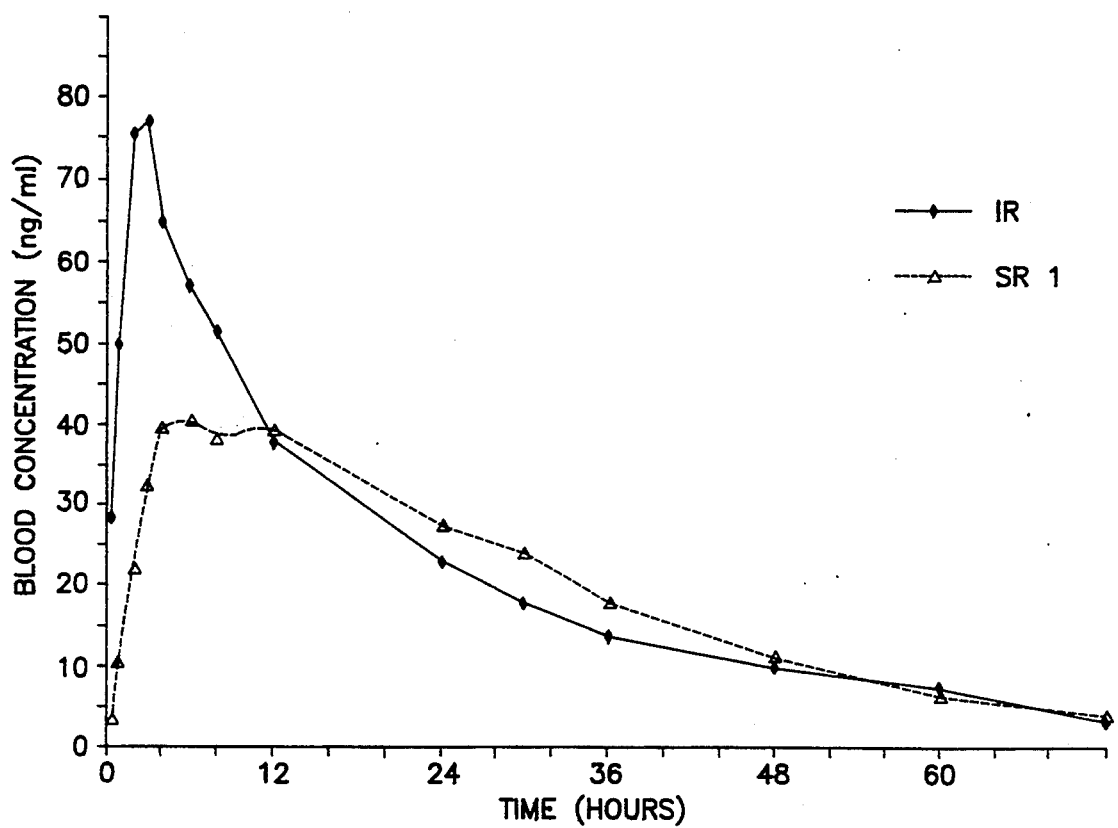
FIG. 2 is a chart showing concentrations of indapamide and comparing an immediate-release form of indapamide and a sustained-release form of indapamide according to the present invention and Example 1 hereof.

The blood concentrations of indapamide were measured in six patients after administration of the SR 1 tablet or of an immediate-release tablet (IR) of a type available on the open market. The mean curve is given in FIG. 2 (appended).

EXAMPLE 2

A sustained-release tablet (SR 2) is prepared by employing the formula given in Table 2, following the operating procedure described in stages A to D.

TABLE 2

Unit formul of the SR 2 tablet

| Compound | Quantity (mg) |
| --- | --- |
| Indapamide | 2.5 |
| Lactose | 114.9 |
| Polyvidone** | 6.2 |
| Methylhydroxypropylcellulose* | 74.0 |
| Magnesium stearate | 2.0 |
| Colloidal silica | 0.4 |

Figure 3:
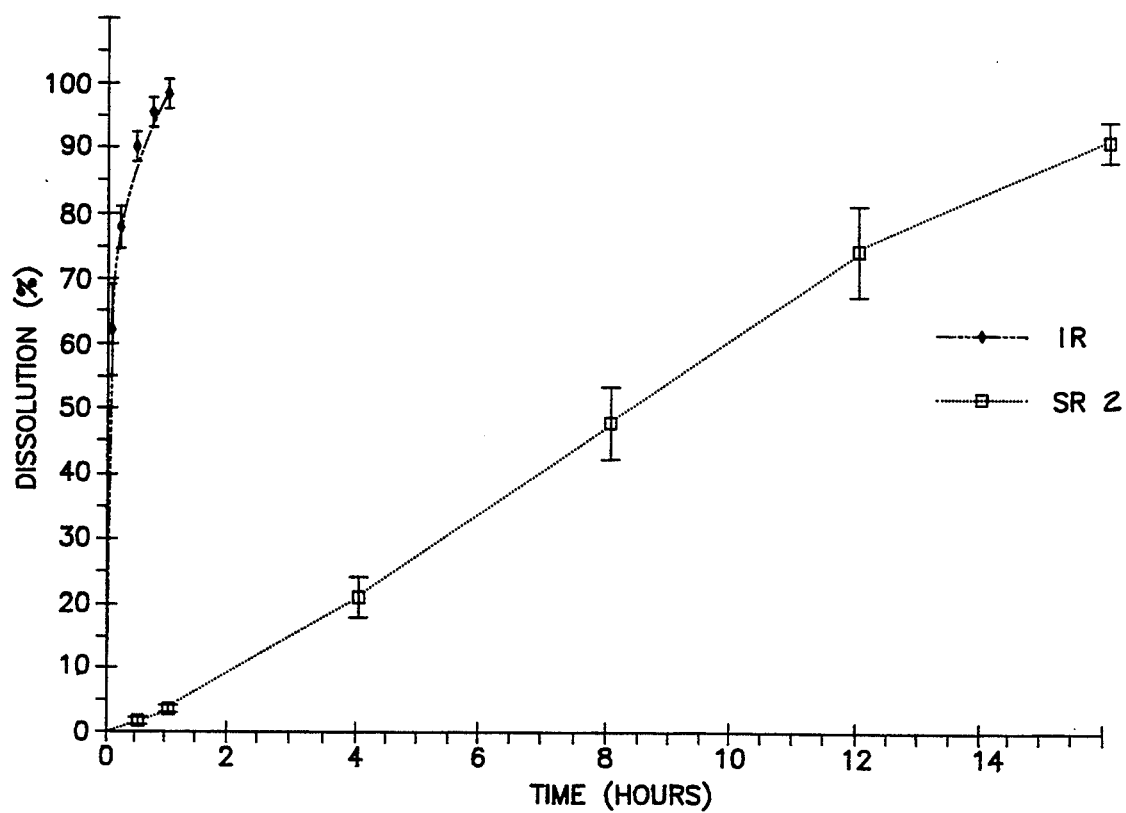
FIG. 3 is a dissolution profile comparing an immediate-release form of an indapamide tablet and a sustained-release form of an indapamide tablet according to the present invention and Example 2 hereof.

The dissolution profile *in vitro* of this form is shown in FIG. 3 (appended).

Figure 4:
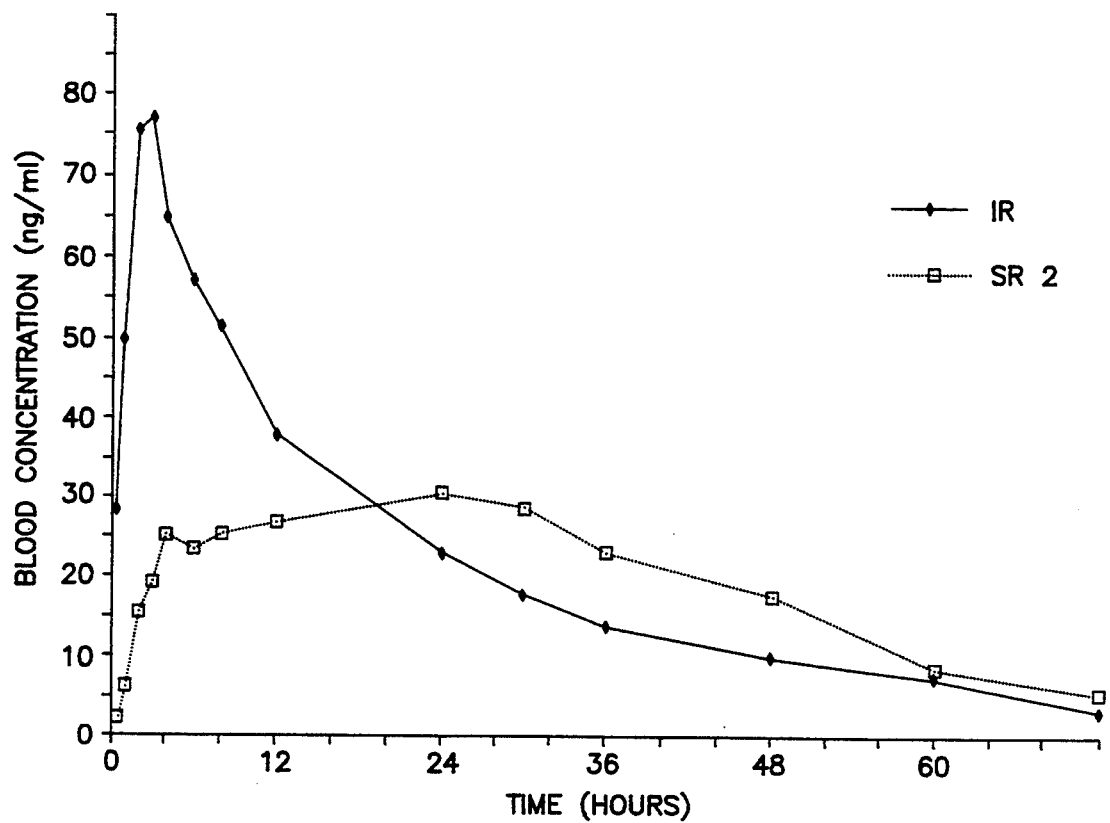
FIG. 4 is a chart showing concentrations of indapamide and comparing an immediate-release form of indapamide and a sustained-release form of indapamide according to the present invention and Example 2 hereof.

The blood concentrations of indapamide were measured in six patients after administration of the SR 2 tablet or of an immediate-release form (IR). The mean curve is given in FIG. 4 (appended).

The comparison between the formulae described in Examples 1 and 2, differing only in the quantity of methyl hydroxypropyl cellulose, shows that it is easy to control the kinetics of dissolution *in vitro* of indapamide. The relationship with the blood kinetics measured in vivo is very good. The two blood kinetics are found to be significantly different.

EXAMPLES 3 TO 5

Three sustained-release tablets (SR 3, SR 4 and SR 5) are prepared by employing the formulae given in Table 3, following the operating process described in stages A to D.

TABLE 3

Unit formula of the SR 3, SR 4 and SR 5 tablets

| Tablet | LP 3 Quantity (mg) | LP 4 Quantity (mg) | LP 5 Quantity (mg) |
| --- | --- | --- | --- |
| Indapamide | 2.0 | 2.0 | 2.0 |
| Lactose | 115.4 | 113.0 | 113.0 |
| Polyvidone** | 6.2 | 8.6 | 8.6 |
| Methylhydroxypropylcellulose* | 74.0 | 74.0 | 59.0 |
| Magnsium stearate | 2.0 | 2.0 | 2.0 |
| Colloidal silica | 0.4 | 0.4 | 0.4 |

*Any high-viscosity methylhydroxyalkylcellulose can be employed, preferably having a viscosity between 1,000 and 20,000 centipoises (cps), preferably about 4,000 cps. Examples employ about 4,000 cps. material.
**Solid polyvidone, MW between 10,000 and 700,000, preferably about 49,000. Examples employ about 49,000 MW material.

Figure 5:
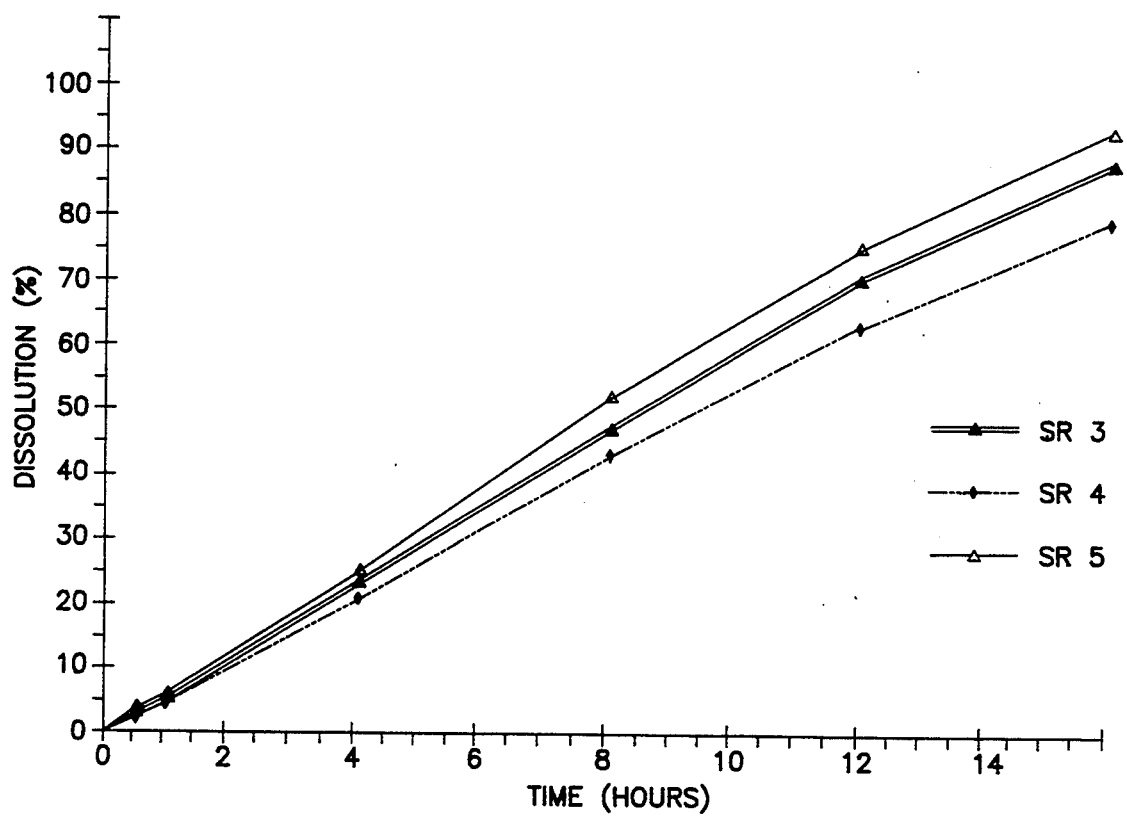
FIG. 5 is a comparison between three sustained-release forms of indapamide according to the present invention and Examples 3, 4, and 5 hereof.

The dissolution profiles *in vitro* of these three forms are shown in FIG. 5 (appended). They show that, by moderating the concentration of each polymer in the formula, it is possible to modulate the release of the active principle.

We claim:

1. A sustained release indapamide matrix tablet consisting essentially of between 1 and 2.5 mg of indapamide, polyvidone, methylhydroxyalkylcellulose, and excipient, which exhibits linear sustained release for at least eight hours, wherein 50 percent of the total quantity of indapamide is released over a period of between 5 and 14 hours, which produces blood levels in humans of between 20 and 80 ng/ml for up to 24 hours after oral administration, produced by a process consisting essentially of the steps of:

(a) mixing indapamide with solid polyvidone having a molecular weight between 10,000 and 700,000 and an excipient;

(b) wetting the mixture of step (a) with an aqueous alcoholic solution to form a granulate;

(c) mixing the granulate with methylhydroxyalkylcellulose having a viscosity between 1,000 and 20,000 centipoises;

(d) lubricating the mixture of step (c) with a lubricating agent; and (e) compressing the lubricated mixture of step (d) in a rotary tableting machine to produce a tablet having a hardness, measured by diametrical crushing, of 60 to 75N, wherein the percentages of indapamide, methylhydroxyalkylcellulose, and polyvidone are respectively approximately 1%, between 30 and 50 percent, and between 2 and 10 percent of the total mass of the tablet, the excipient consisting essentially of a compound selected from the group consisting of sugar, colloidal silica, and lubricant.

2. The method of treating essential arterial hypertension for which indapamide is known to be effective which comprises the step of administering orally to a patient, an effective antihypertensive amount of a matrix tablet for the sustained release of indapamide of claim 1.

3. The matrix tablet of indapamide as claimed in claim 1, wherein the methylhydroxyalkylcellulose is methylhydroxypropylcellulose.

4. The method of delivering indapamide to a patient in need thereof comprising the step of orally administering to said patient a matrix tablet for the sustained release of indapamide according to claim 3.

5. A matrix tablet of claim 1, wherein the pharmaceutically-acceptable excipients are selected from the group consisting of lactose, colloidal silica, and lubricant.

6. The method of delivering indapamide to a patient in need thereof comprising the step of orally administering to said patient a matrix tablet for the sustained release of indapamide according to claim 5.

7. A process for producing a sustained release matrix tablet of indapamide consisting essentially of between 1 and 2.5 mg of indapamide, polyvidone, methylhydroxyalkylcellulose, and excipient, and exhibiting linear sustained release for at least eight hours, wherein 50 percent of the total quantity of indapamide is released over a period of between 5 and 14 hours to produce blood levels in humans of between 20 and 80 ng/ml for up to 24 hours after oral administration, consisting essentially of the steps of:

(a) mixing indapamide with solid polyvidone having a molecular weight between 10,000 and 700,000 and an excipient;

(b) wetting the mixture of step (a) with an aqueous alcoholic solution to form a granulate;

(c) mixing the granulate with methylhydroxyalkylcellulose having a viscosity between 1,000 and 20,000 centipoises;

(d) lubricating the mixture of step (c) with a lubricating agent; and (e) compressing the lubricated mixture of step (d) in a rotary tableting machine to produce a tablet having a hardness, measured by diametrical crushing, of 60 to 75N;

wherein the percentages of indapamide, methylhydroxylalkylcellulose, and polyvidone are respectively approximately 1%, between 30 and 50 percent, and between 2 and 20 percent of the total mass of the tablet, the excipient consisting essentially of a compound selected from the group consisting of sugar, colloidal silica, and lubricant.

8. The method of claim 7, wherein the high-viscosity methylhydroxyalkylcellulose is methylhydroxypropylcellulose.

9. The method of claim 7, wherein the pharmaceutically-acceptable excipients are selected from the group consisting of lactose, colloidal silica, and lubricant.

* * * * *

UNITED STATES PATENT AND TRADEMARK OFFICE
CERTIFICATE OF CORRECTION

PATENT NO. : 5,334,392

DATED : August 2, 1994

INVENTOR(S) : Alain Cuine, Bruno H. de Barochez, David Guez

It is certified that error appears in the above-indentified patent and that said Letters Patent is hereby corrected as shown below:

```
Column  6, line 13; "droxylalkylcellulose" should read
     -- droxyalkylcellulose --
Column  6, line 19; delete the words "high-viscosity"
```

Signed and Sealed this

Fifteenth Day of November, 1994

Attest:

BRUCE LEHMAN

Attesting Officer     Commissioner of Patents and Trademarks